US006573097B2

(12) United States Patent
Cantrell et al.

(10) Patent No.: US 6,573,097 B2
(45) Date of Patent: *Jun. 3, 2003

(54) METHOD OF FERTILIZING AN AVIAN EGG IN THE SHELL

(75) Inventors: Tim Cantrell, Gainesville, GA (US); Andrew Wooten, Athens, GA (US)

(73) Assignee: Ovo Biosciences, Inc., Athens, GA (US)

( * ) Notice: Subject to any disclaimer, the term of this patent is extended or adjusted under 35 U.S.C. 154(b) by 50 days.

This patent is subject to a terminal disclaimer.

(21) Appl. No.: 09/784,803

(22) Filed: Feb. 15, 2001

(65) Prior Publication Data

US 2001/0027569 A1 Oct. 4, 2001

Related U.S. Application Data

(60) Provisional application No. 60/182,432, filed on Feb. 15, 2000, and provisional application No. 60/182,969, filed on Feb. 16, 2000.

(51) Int. Cl.$^7$ ............................. C12N 5/06; A01K 45/00
(52) U.S. Cl. ......................... 435/349; 435/345; 119/6.8
(58) Field of Search ............................... 435/349, 345; 119/6.8

(56) References Cited

U.S. PATENT DOCUMENTS

| | | | | |
|---|---|---|---|---|
| 4,378,758 A | * | 4/1983 | Coleman | 119/35 |
| 4,903,635 A | * | 2/1990 | Hebrank | 435/284 |
| 5,136,979 A | | 8/1992 | Paul et al. | |
| 5,158,038 A | | 10/1992 | Sheeks et al. | |
| 5,176,101 A | | 1/1993 | Paul et al. | |
| 5,339,766 A | | 8/1994 | Phelps et al. | |
| 5,438,954 A | | 8/1995 | Phelps et al. | |
| 5,529,792 A | * | 6/1996 | Risau et al. | 424/570 |
| 5,699,751 A | | 12/1997 | Phelps et al. | |
| 5,722,342 A | | 3/1998 | Line et al. | |
| 5,900,929 A | | 5/1999 | Hebrank et al. | |

FOREIGN PATENT DOCUMENTS

| | | |
|---|---|---|
| FR | 2 623 206 | 5/1989 |
| WO | WO 93/14629 | 8/1993 |
| WO | WO 93/15185 | 8/1993 |

OTHER PUBLICATIONS

Johnston et al. "In vitro sperm binding, penetration and fertilization of recently oviposited chicken eggs". Poultry Science, (1998), vol. 77, No. Suppl. 1, p. 142.*

Ono et al. "Mineral content of quail embryo cultured in mineral–rich and mineral–free conditions". Poultry Science. 1984. vol. 63, pp. 159–166.*

Sarvella, "Sporadic Occurrence of Parthenogenesis" *Journal Of Heredity*, 61(5):215–219 (1970).

Sarvella, "Development of Parthenogenesis in Chickens" *Poultry Science*, 50(5):1626 (1971).

Sherman et al. "Transposition of the Drosophila element mariner into the chicken germ line" *Nature Biotechnology* 16(11): 1050–1053, 1998.

Johnston, SC "In vitro Sperm Binding, Penetration, and Fertilization of Recently Oviposited Chicken Eggs" Thesis, Graduate School of Clemson University, Dec., 1998.

Bakst et al. "Effects of Isolation and Culture of Turkey Primary Follicular Oocytes on Morphology and Germinal Vesicle Integrity" *Theriogenology* 50: 1121–1130, Nov., 1998.

Cibelli et al. "Cloned Transgenic Calves Produced from Nonquiescent Fetal Fibroblast" *Science* 280: 1256–1258, May 22, 1998.

Wakayama et al. "Full–term development of mice from enucleated oocytes injected wit cumulus cell nuclei" *Nature* 394: 369–374, Jul. 23, 1998.

Kuroki et al. "Binding of Spermatozoa to the Perivitelline Layer in the Presence of a Protease Inhibitor" *Poult Sci.* 5: 748–752, May, 1997.

Etches and Gibbins "Strategies for the Production of Transgenic Chickens" *Methods Mol Biol.* 62:433–450, 1997.

Love et al. "Transgenic Birds by DNA microinjection" *Biotechnology* 12: 60–63, Jan., 1994.

Tanaka et al. "Chicken Production by in vitro fertilization of the fowl ovum" *J. Reprod. Fert.* 100: 447–449, 1994.

Petitte et al. "Blastodermal Cell Transfer and Germine Chimeras" in *Manipulation of the Avian Genome* (RC Press Boca Raton, FL 84–85, 1993.

Bakst, MR "Artificial Insemination Technology" in *Manipulation of the Avian Genome* (RC Press Boca Raton, FL 24–26, 1993.

Barnes et al. "Influence of Recipient Oocyte Cell Cycle Stage on DNA Synthesis, Nuclear Envelope Breakdown, Chromosome Constitution, and Development in Nuclear Transport Bovine Embryos" *Molecular Reproduction and Development* 36:33–41, 1993.

Vick et al. "Transgenic birds from transformed primordial germ cells" *Proc R Soc Lon B Biol Sci.* 251(1332): 179–182, Mar. 22, 1993.

Sang et al. "Transfection of Chick Embryos Maintained Under in Vitro Conditions" in *Manipulation of the Avian Genome* (RC Press 121–133, 1993.

(List continued on next page.)

*Primary Examiner*—Sandra E. Saucier
*Assistant Examiner*—Vera Afremova

(57) ABSTRACT

The present invention relates to the field of avian egg fertilization. In particular, the present invention provides a method of fertilizing an egg in a shell. The invention also provides a method of fertilizing an egg in a shell, whereby a live chick is hatched. The invention also provides developmentally early stage oviposited avian eggs.

49 Claims, No Drawings

OTHER PUBLICATIONS

Campbell et al. "Nuclear–Cytoplasmic Interactions during the First Cell Cycle of Nuclear Transfer Reconstructed Bovine Embryos: Implications for Deoxyribonucleic Acid Replication and Development" *Biology of Reproduction* 49, 933–942, 1993.

Nakanishi and Iritani "Gene Transfer in the Chicken by Sperm–Mediated Methods" *Mol Reprod Dev.* 36(2):258–261, Oct. 1993.

First et al. "Use of in Vitro Matured Oocytes 24 HR of Age in Bovine Nuclear Transfer" *Theriogenology* 37(1): 211, 1992.

Yang et al. "Improved Activation by Combined Cycloheximide and Electric Pulse Treatment of Bovine Follicular Oocytes Matured in Vitro for 23–24 Hours" Biol Reprod. 46 (Suppl 1): 117, 1992.

Fissore and Robl "Intracellular $Ca^{2+}$ Response of Rabbit Oocytes to Electrical Stimulation" *Mol Reprod Dev.* 32: 9–16, 1992.

Kline and Kline "Repetitive Calcium Transients and the Role of Calcium in Exocytosis and Cell Cycle Activation in the Mouse Egg" *Dev Biol.* 149:80–89, 1992.

Rickords and White "Electrofusion–Induced Intracellular $Ca^{a+}$ Flux and its Effect on Murine Oocyte Activation" *Mol Reprod Dev.* 31:152–159, 1992.

Stice and Keefer "Improved Developmental Rates for Bovine Nucleus Transfer Embryos Using Cold Shock Activated Oocytes" *Biol Reprod.* 462(Suppl 1): 166, 1992.

Tombes et al. "Meiosis, Egg Activation and Nuclear Envelope Breakdown Are Differentially Reliant on $Ca^{2+}$, Whereas Germinal Vesicle Breakdown Is $Ca^{2+}$ Independent in the Mouse Oocyte" *J Cell Biol.* 117: 799–811, 1992.

Nakanishi et al. "Fertilizing Competency of Multiple Ovulated Eggs in the Domestic Fowl (*Gallus domesticus*)" *Mol Reprod Dev.* 28(2):131–135, Feb., 1991.

Fulka et al. "Effect of 6–Dimethylaminopurine on Germinal Vesicle Breakdown of Bovine Oocytes" *Mol Reprod Dev.* 29: 379–384, 1991.

Susko–Parrish et al. "Effect of Bovine Oocyte Aging in Vitro on Development" *Biol Reprod.* 44(Suppl 1): 17:156 (abstract), 1991.

Watanabe et al. "Independent inactivation of MPF and cytostatic factor (Mos) upon fertilization of Xenopus eggs" *Nature* 352: 247–248, 1991.

Yang et al. "Nuclear Transfer in Rabbits and Cattle by Electric Pulse–Induced Fusion of Blastomeres to Enucleated Oocytes" *Theriogenology* 35(1): 298 (abstract), 1991.

Shuman RM "Production of transgenic birds" *Experientia* 47(9): 897–905, Sep. 15, 1991.

Nakanishi et al. "Early Nuclear Events in Vitro Fertilization in the Domestic Fowl (*Gallus domesticus*" *Mol Reprod Dev.* 26(3): 217–221, Jul. 1990.

Bakst, MR "Preservation of Avian Cells" *Developments in Animal Veterinary Sciences* 22: 91–108, 1990.

Collas and Robl "Factors Affecting the Efficiency of Nuclear Transplantation in the Rabbit Embryo" *Biol Reprod.* 43: 877–884, 1990.

Landa and Hajkova "Diploidization of Bovine Oocytes Matured in Vitro and Parthenogenetically Activated by Electric Shock" *Folia Biologica* 36: 145–152, 1990.

Nurse, P "Universal control mechanism regulating onset of M–phase" *Nature* 344: 503–508, 1990.

Ozil, JP "The parthenogenetic development of rabbit oocytes after repetitive pulsatile electrical stimulation" *Development* 109: 117–127, 1990.

Stice and Robl "Activation of Mammalian Oocytes by a Factor Obtained from Rabbit Sperm" *Mol. Reprod. Dev.* 25:272–280, 1990.

Swann, K "A cytosolic sperm factor stimulates calcium increases and mimics fertilization in hamster eggs" *Development* 110: 1295–1302, 1990.

Yang et al. "Potential of Hypertonic Medium Treatment for Embryo Micromanipulation: II. Assessment of Nuclear Transplantation Methodology, Isolation, Subzona Insertion, and Electrofusion of Blastomeres to Intact or Functionally Enucleated Oocytes in Rabbits" *Mol Reprod Dev.* 27: 118–129, 1990.

Petitte et al. "Production of somatic and germline chimeras in the chicken by transfer of early blastodermal cells" *Development* 108, 185–189, 1990.

Bosselman et al. "Germline Transmission of Exogenous Genes in the Chicken" *Science* 243: 533–535, 1989.

Wentworth et al. "Manipulation of Avian Primordial Germ Cells and Gonadal Differentiation" *Poultry Sci.* 68: 999–1010, 1989.

Ware et al. "Age Dependence of Bovine Oocyte Activation" *Gamete Res.* 22: 265–275, 1989.

Kubiak, J "Mouse Oocytes Gradually Develop the Capacity for Activation During the Metaphase II Arrest" *Dev Biol.* 136: 537–545, 1989.

Onodera and Tsunoda "Parthenogenetic Activation of Mouse and Rabbit Eggs by Electric Stimulation In Vitro" *Gamete Research* 22: 277–283, 1989.

Watanabe et al. "Specific proteolysis of the c–mos proto–oncogene product by calpain on fertilization of Xenopus eggs" *Nature* 342: 505–510, Nov. 30, 1989.

Sirard et al. "The Culture of Bovine Oocytes to Obtain Developmentally Competent Embryos" *Biol Reprod.* 39:546–552, 1988.

Nagai, T "Parthogenetic Activation of Cattle Follicular Oocytes in Vitro with Ethanol" *Gamete Res.* 16:243–249, 1987.

Thomas and Capecchi "Site Directed Mutagenesis by Gene Targeting in Mouse Embryo–Derived Stem Cells" *Cell* 51, 503–512, 1987.

Salter et al. "Gene Insertion into the Chicken Germ Line by Retroviruses" *Poul. Sci.* 65: 1445–1458, 1986.

Whitaker and Irvine "Inositol 1, 4, 5–trisphophate microinjection activates sea urchin eggs" *Nature* (London) 312: 636–639, Dec. 13, 1984.

Bradley et al. "Formation of germline chimeras from embryo–derived teratocarcinoma cell lines" *Nature* (London), 309: 255–256, May 17, 1984.

Eusebi and Siracusa "An Electrophysiological Study of Parthenogenetic Activation in Mammalian Oocytes" *Developmental Biology*, 96:386–395, 1983.

Cuthbertson, KSR "Parthenogenetic Activation of Mouse Oocytes in Vitro with Ethanol and Benzyl Alcohol" *J Exp Zool.* 226: 311–314, 1983.

Alberts et al. "Egg Activation Is Mediated by Changes in Intracellular Ion Concentrations[16,19]" *Molecular Biology of the Cell* 804–809, 1983.

McGrath and Solter "Nuclear Transplantation in the Mouse Embryo by Microsurgery and Cell Fusion" *Science* 220: 1300–1302, 1983.

Martin, G "Isolation of a pluriopoten cell line from early mouse embryos cultured in medium conditioned by teratocarcinoma stem cells" *Proc Nat Acad Sci.* 78: 7634–7638, 1981.

Koyanagi and Nishiyama "Fate of Spermatozoa That Do No Participate in Fertilization in the Domestic Fowl" *Cell Tissue Res* 214: 89–95, 1981.

Kaufman, "Parthenogenesis: a system facilitating understanding of factors that influence early mammalian development" *Prog. in Anat.* 1: 1–34, 1981.

Evans and Kaufman "Establishment in culture of pluripotential cells from mouse embryos" *Nature* (London), 292: 154–156, 1981.

Siracusa et al. "Parthenogenetic activation of mouse oocytes induced by inhibitors of protein synthesis" *J. Embryol. Exp. Morph.* 43:157–166, 1978.

Okamura and Nishiyama "The Passage of Spermatozoa through the Vitelline Membrane in the Domestic Fowl, *Gallus gallus*" *Cell Tiss. Res.* 188: 497–508, 1978.

Bakst and Howarth, Jr. "Hydrolysis of the Hen's Perivitelline Layer by Cock Sperm in vitro" *Biol Reprod.* 17:370–379, 1977.

Surani and Kaufmann "Influence of Extracellular $Ca^{2+}$ and $Mg^{2+}$ Ions of the Second Meiotic Division of Mouse Oocytes: Relevance to Obtaining Haploid and Diploid Parthenogenetic Embryos" *Dev Biol.* 59:86–90, 1977.

Maeza and Buss "Sperm Concentration and Sperm Numbers as Related to Fertility in Chickens" *Poultry Science* 55(5): 2059, 1976.

Tarkowski, AK "Induced Parthenogenesis in the Mouse" *The Developmental Biology of Reproduction* (C.L. Market, E.J. Papaconstantinon, eds.) 107–129, New York: Academic Press, 1975.

Steinhardt, et al. "Is calcium ionophore a universal activator for fertilized eggs?" *Nature* 252: 41–43, 1974.

Masui and Markert "Cytoplasmic Control of Nuclear Behavior during Meiotic Maturation of Frog Oocytes" *J Exp Zool.* 177: 129–146, 1971.

Tarkowski et al. "Experiment Parthenogenesis in the Mouse" *Nature* 226: 162–165, 1970.

Olsen, MW "Maturation, Fertilization, and Early Cleavage in the Hen's Egg" *J Morph* 70: 513–533, 1942.

* cited by examiner

METHOD OF FERTILIZING AN AVIAN EGG IN THE SHELL

This application claims priority to U.S. provisional application Ser. No. 60/182,432, filed Feb. 15, 2000, and U.S. provisional patent application Ser. No. 60/182,969, filed Feb. 16, 2000.

BACKGROUND OF THE INVENTION

1. Field of the Invention

The present invention relates to the field of avian egg fertilization. In particular, the present invention relates to a method of fertilizing an egg in a shell.

2. Background Art

TRADITIONAL BREEDING

Typically, breeding in the poultry industry is carried out by either one of two systems:

Floor Breeding Program

The first system is called "floor breeding" and it is utilized to produce the vast majority of all commercial hatching eggs. In this system males are simply added into the flocks of females at a typical ratio of between 10 and 15 percent. The floor breeding system, even with its inefficiencies, is currently the low-cost system for producing hatching eggs because it requires less labor than competing systems. Average hatch rates range from approximately 83% for broiler breeders to 92% for layer breeders. Even though this system has been the backbone of the poultry industry for many years, it has many limitations.

Size Versus Reproductive Capacity

Floor breeding is no longer practiced at all in turkeys due to the intense selection for increased muscle yield that has rendered commercial turkey breeds incapable of natural mating. The same trend is being seen in broilers. Selection for increased size in broilers has compromised fertility and mating ability and it is predicted that fertility will continue to decline as body weights increase. This presents a dilemma for poultry producers because decreases in fertility have a direct negative impact on their bottom line.

Inefficient Waste Removal

Natural mating must be performed on solid floors to avoid injury to the birds. This design requirement precludes the use of automated waste removal systems and necessitates manual cleaning between successive flocks of birds. This adds to labor and overhead costs while decreasing the productive use of facilities.

Egg Production & Quality

Since eggs remain in the houses with the flock until collection time; eggs are frequently contaminated with dirt and fecal material which can reduce hatch rates. In addition, typically between 3 and 5% of the eggs produced in floor houses are laid directly on the floor rather than in the provided laying boxes and must be discarded.

Inefficient Space and Equipment Utilization

Maintaining males and females together in a floor house requires the installation of two independent feed and watering systems because of different nutritional and production requirements for each sex. It also requires the installation of laying boxes and automated egg collection systems. All of this equipment occupies limited floor space in the house. For these reasons floor rearing is not an efficient use of housing space and equipment when compared to stacked cage systems.

Mortality & Fertility

Aggressive males tend to fight, leading to higher male mortality rates. Male mortality rates average 13% in floor houses versus 2% in cage houses. Male aggressiveness towards hens during mating gradually takes a toll in the form of increased female mortality, decreased fertility, and a decrease in the length of the egg production cycle. As the males in one flock get older, fertility starts to decline. The standard solution is to "spike" the flock with young males to improve fertility. However, this sets off another round of aggression with a short-term decrease in fertility and an increase in mortality. Disease is more common in floor houses because of the constant contact of the birds with bedding and waste material that harbor pathogenic organisms.

Decreased Feed Conversion

Controlling feed costs is critical to running a competitive poultry operation. Feed costs can account for up to 60% of the cost of raising a broiler chick, for instance. In one study, birds raised on the floor consumed 20% more food for the same amount of production when compared to those raised in cages. This difference is due to the increased level of social interactions as well as the generally higher level of physical activity seen in floor houses. Males consume more feed than females, making the floor breeding system inefficient with respect to feed consumption due to the large numbers of males that must be maintained.

Limited Flexibility in Breeding Strategies

Due to the fact that males and females are housed in one large group in the floor breeding house arrangement, the breeder is very restricted in their ability to perform advanced crosses and selections on the breeding stock. For this reason floor houses are primarily utilized as a tool for the multiplication of pre-selected genetic stocks to produce final commercial crosses.

Artificial Insemination Breeding Program

Another system utilized to generate hatching eggs is called artificial insemination (AI). AI is widely practiced by "primary breeders" at the top of the breeding pyramid but not generally used by commercial producers at the bottom of the pyramid. Primary breeders are companies that own and improve the elite pedigreed genetic lines that are crossed to produce the final commercial products-broilers, layers and turkeys. The quantities of birds increase exponentially as you move down the breeding pyramid from the pedigreed lines through the grandparent stock, parent stock, and finally to the actual commercial birds. While birds of elite genetic makeup at the top of the pyramid are very expensive, birds at the bottom are inexpensive. For these reasons, different operational models are utilized for reproduction at different level.

In the AI system, males and females are housed in the same houses but are caged separately. The female cages typically hold between two and five hens, while the male cages hold a single rooster. AI programs address many of the limitations of the floor breeding houses listed above. For example, since cage houses are utilized, waste removal can be performed automatically. Houses are generally much cleaner, leading to fewer disease problems. Egg production is improved because eggs roll out of the cages and is not laid on dirty floors. Equipment and housing space are utilized more efficiently. Mortality is minimized due to a decrease in social aggression and disease. Fertility levels are maintained more consistently because social and physical interaction are eliminated from the process of reproduction. Feed conversion is increased. And finally, the production system has increased flexibility for doing advanced crosses and selections. This capability is absolutely required by primary breeders in order to improve their genetic stocks and to stay competitive in the marketplace. While most of the advantages listed above are also important for commercial-level multiplication breeders, they are offset by one crucial shortcoming, the high labor costs associated with AI programs.

AI programs replace the innate sexual drive of poultry with human labor. Workers must manually collect semen from males in cages and inseminate females in cages on a 7-day rotation. The level of sophistication required in these programs mandates a skilled workforce. For this reason, the AI program, though operationally superior, is economically impractical for commercial-level breeding programs. Even the use of dwarf hens, an innovation that allows similar egg production with about 30% less feed consumption, can not justify the increased labor costs of the AI program for commercial level multiplication breeders.

REPRODUCTIVE PROCESS

At the time of ovulation, the avian oocyte comprises a blastodisc, or germinal disc, which contains the female pronucleus, and a yellow yolk mass. The germinal disc and yolk mass are surrounded by the oocyte cell membrane, called the oolemma. Surrounding the oolemma is the perivitelline layer (PL), also referred to as the inner perivitelline layer (IPL). The space between the oolemma and the IPL is termed the perivitelline space, which is traversed by granulosa cells. Once the oocyte is released from its ovarian follicle, it is referred to as an ovum. The ovum moves into the oviduct where it is engulfed by the infundibulum, where fertilization occurs if sperm are present.

As the ovum passes into the posterior infundibulum, another layer, the outer perivitelline layer (OPL), surrounds the ovum. This membrane acts to prevent polyspermy, which is a lethal condition that occurs when multiple sperm bind to and penetrate the ovum at the region of the blastodisc (Koyanagi et al., "Fate of spermatozoa that do not participate in fertilization," Cell Tissue Res., 1981; 214 (1): 89–95; Okamura et al., "The passage of spermatozoa through the vitelline membrane in the domestic fowl Gallus gallus," Cell Tissue Res., 1978; 188(3): 497–508; Bakst et al., "Hydrolysis of the Hen's Perivitelline Layer by Cock Sperm in vitro," Biol. Reprod., 17: 370–379). The egg is then surrounded with additional layers of chalaza and thick and thin layers of albumen. When the ovum moves into the isthmus, two shell membranes are deposited, upon which small crystals of calcium carbonate are deposited, thus beginning the formation of the shell.

The preceding events all occur within the first few hours following fertilization. The ovum next moves into the uterus, where over the next 18–20 hours, the calcium shell is completed. The egg then moves into the vagina for several minutes, and then is extruded from the vagina, or oviposited (i.e., "laid"). At this point, if the egg has been fertilized, the embryo contained therein will have 40,000 to 70,000 cells. (Johnston ("In Vitro Sperm Binding, Penetration, and Fertilization of Recently Oviposited Chicken Eggs," December 1988, Clemson University); Olsen, M. W., J. Morph. 70: 413–533 (1942); Etches et al., in Methods in Molecular Biology, vol. 62 *Recombinant Gene Expression Protocols*, Ed. R. Tuan, Humana Press, Inc. Totowa, N.J., pp. 433–450 (1997); Petitte et al., in Manipulation of the Avian Genome, Ed. Etches et al., CRC Press, Boca Raton, Fla., pp. 81–101 (1993)).

The present invention provides a ground-breaking improvement in avian biology by making it possible to fertilize an oviposited egg in its shell, to obtain embryo development, and to hatch a live bird from the shell, herein called "in ovo fertilization," (IOF). Such methods provide an alternative to floor breeding and IV fertilization that can greatly increase the efficiency of poultry production.

SUMMARY OF THE INVENTION

The present invention relates to the field of avian egg fertilization. In particular, the present invention provides a method of fertilizing an egg in a shell. The invention also provides a method of fertilizing an egg in a shell, whereby a live chick is hatched. The invention also provides developmentally early stage oviposited avian eggs.

DETAILED DESCRIPTION OF THE INVENTION

As used herein, "a," "an" or "the" may mean one or more. For example, "an" egg may mean one egg or more than one egg. Moreover, "the" egg may mean one egg or more than one egg.

The present invention provides a method of fertilizing an avian egg in a shell, wherein the egg comprises a yolk enclosed by a membrane, comprising obtaining a sperm sample comprising avian sperm in a physiologically acceptable carrier, and delivering the sperm sample into the egg, so as to fertilize the egg. The present invention relates to the unexpected and surprising discovery that an unfertilized, oviposited avian egg can be fertilized in the shell and produce a live chick. As used herein, reference to an avian egg in a shell refers to an oviposited egg, that is, an egg with a calcium carbonate shell that has been extruded from the vagina of the bird. Extrusion of the egg is referred to as "oviposition." Accordingly, all references herein to an "egg in a shell" or to an "oviposited egg" should be understood to be equivalent in meaning. The process of fertilizing an oviposited egg in a shell is referred to herein as "in ovo fertilization" (IOF).

An avian egg comprises a hard, calcified shell at the time the egg is oviposited. Within the shell is a yolk that contains nutrients for supporting growth and development of an embryo. As used herein, an "embryo" is a developing organism resulting from the joining of a female pronucleus and a male pronucleus during the process of egg fertilization. While a fertilized (single cell) ovum may thus be called an embryo, the single cell embryo is also specifically referred to herein as a zygote.

Although in ovo fertilization can be performed on eggs as old as 2 weeks if the eggs are maintained at room temperature, ideally newly oviposited eggs are used for the best results. In a preferred embodiment, the sperm sample is delivered into the egg between 0 and 96 hours following oviposition. In a more preferred embodiment, the sperm sample is delivered into the egg between 0 and 72 hours following oviposition. In an even more preferred embodiment, the sperm sample is delivered into the egg between 0 and 48 hours following oviposition. In a highly preferred embodiment, the sperm sample is delivered into the egg between 0 and 24 hours following oviposition. Thus, it is preferred that the sperm sample be delivered into the egg as soon as possible following oviposition. However, the precise timing of fertilization can depend on how the oviposited egg is maintained, e.g., temperature, humidity, etc. For example, fertilization can improve if the unfertilized oviposited egg is fertilized before it is allowed to cool.

The sperm in the sperm sample may be obtained from a bird by methods known to a person skilled in the art, such as the abdominal massage method which is well-known to those of skill in the art. This method allows the collection of an ejaculate (semen) comprising sperm, seminal fluid, and transparent fluid. Transparent fluid is a lymphlike fluid that passes from the lymph channels to the surface of the phallus during phallic tumescence. Avian sperm may also be obtained from commercial sources that are well known to those of skill in the art.

In one embodiment, the sperm in the sperm sample is from a single bird. In another embodiment, the sperm in the sperm sample is a mixture of sperm obtained from more than one bird. When a mixture of sperm from more than one bird is used in the methods of the invention, the probability of successfully fertilizing the egg can increase, because if one of the birds from which the sperm has been collected is infertile, it is possible that the sperm collected from the other bird or birds will be capable of fertilizing the egg.

In a preferred embodiment, the sperm sample comprises sperm from birds which are members of the same species, and the sperm sample is used to fertilize eggs oviposited by hens which are members of the same species as the sperm donors. The present invention also contemplates the use of sperm from one species and an egg from another species, if the sperm is capable of fertilizing the egg.

While it is typically preferred that the sperm be used within 30 minutes of the time that it is collected, older sperm, and even sperm which have previously been frozen or freeze dried may be used in the methods of the invention, as long as the sperm retain their ability to fertilize an ovum. Where the sperm are to be used more than 30 minutes after collection, it is preferred that they be combined with a sperm extender, as is described below.

As mentioned above, the sperm sample also comprises a physiologically acceptable carrier. As used herein, a "physiologically acceptable carrier" is a fluid in which sperm remain motile and viable. Examples of a physiologically acceptable carrier include, but are not limited to, unaltered semen, seminal fluid (either original to the sperm or added), transparent fluid (either original to the sperm or added), buffered saline solution, sperm extender, and combinations thereof. Preferably, the carrier includes sperm extender, also referred to in the art as a diluent. As mentioned above, the use of a sperm extender is especially preferred where the collected sperm will not be used for fertilization within 30 minutes after collection. M. R. Bakst, In *Manipulation of the Avian Genome*, R. J. Etches and AM. Verrinder Gibbons, eds., CRC Press, Boca Raton, Fla., pp. 15–28 (1993). As used herein, a "sperm extender" is a physiologically acceptable carrier that is used to dilute a sperm sample to produce a sperm sample of greater volume in which the sperm are less concentrated. Preferably, the composition of the sperm extender will extend the shelf life of the sperm, as well as diluting the sperm so as to increase the number of eggs which may be fertilized by the quantity of sperm which has been collected. Examples of sperm extender compositions, suggested dilution rates, optimal storage times and conditions, and commercial sources of extender may be found in Bakst ("Preservation of Avian Cells: *In: Poultry breeding and Genetics*, R. D. Crawford (ed.) Elsevier, N.Y., pp 91–108 (1990)). Other diluents commonly used in the poultry industry are Lago Formulation Avian Semen Extender by Hygeia Biological Laboratories, Semaid Turkey Extender by Poultry Health Laboratories in Davis Calif., Beltsville Poultry Semen Extender by Tri Bio Laboratories, Inc. in State College, Pa. In a preferred embodiment, the sperm extender is Avidiluent. Avidiluent is produced by IMB, 10 rue Georges, Clemenceau, BP 81, 61302 1' Aigle, France.

Thus, in one embodiment, the sperm sample may comprise sperm and seminal fluid, i.e., semen. Moreover, the sperm sample may comprise sperm and seminal fluid which is diluted with a physiologically acceptable carrier, including but not limited to buffered saline solution and a sperm extender.

The sperm sample can also be prepared by methods which will be clear to one of ordinary skill in the art, such as washing semen from one or more birds with a solution such as buffered saline solution or sperm extender, centrifuging the resulting solution, removing the supernatant, and resuspending the washed sperm in a volume of a solution such as buffered saline or semen extender. One of ordinary skill in the art will readily understand how to achieve the desired concentration of sperm by resuspending the sperm in the appropriate volume of solution. For example, following centrifugation and removal of supernatant, the packed sperm may then be weighed, and the number of sperm then estimated by using known values for the weight of avian sperm. The sperm may then be resuspended in the volume required to obtain the desired sperm concentration. Alternatively, the centrifuiged sperm may be resuspended following removal of the supernatant, and then recentrifuiged, allowing the determination of the packed sperm volume. (Johnston S., "In Vitro Sperm Binding, Penetration, and Fertilization of Recently Oviposited Chicken Eggs," M. S. Thesis presented to the Graduate School of Clemson University, 1998). Subsequently, the concentration of the sperm may be calculated using the formula of Maeza and Buss. (Poultry Sci. 55:2059 (1976)).

Typically, the concentration of sperm in chicken semen is from 300 million to 800 million per milliliter, in turkey semen from 800 million to 1.5 billion per milliliter, in Guinea fowl semen from 400 million to 800 million per milliliter, in Pekin duck semen from 20 million to 600 million per milliliter. The standard number of sperm used for artificial insemination is 100 million in a total volume of 50 micro liters. In the methods of the present invention, because sperm are placed directly adjacent to the female pronucleus, far fewer sperm are required to fertilize the egg. Thus, as few as one sperm can be used in the methods of the present invention. In fact, a large range of sperm concentrations can be used in the present invention. In one embodiment, chicken semen is diluted with an equal volume of Avidiluent and approximately 0.01 milliliters of this sperm sample is injected into an egg. Thus, approximately 1 million sperm would be deposited adjacent to the female pronucleus.

In the methods of the invention, fertilization of the avian egg in the shell is accomplished by delivering the sperm sample into the egg. Delivery of the sperm sample may be accomplished by any method which will allow the sperm to be delivered inside the shell, including, but not limited to, dissolving an area of the shell with, e.g., an acid solution, using electroporation, and creating an opening by penetrating or cracking an area of the shell, for example using a tool such as a needle or a scalpel.

Preferably, the surface of the area of the shell to be penetrated in order to deliver the sperm sample is sanitized before the sperm is delivered inside, to prevent contamination of the egg. Any method which is compatible with the delivery method may be used to sanitize the shell, including, but not limited to, the disinfectant IOFEC-20®, and 3% hydrogen peroxide. The surface of the egg at the intended penetration site may be wiped or sprayed with the disinfectant, or the egg may be immersed in a vessel containing the disinfectant of choice.

As is described above, an opening in the shell can be made with a tool such as a knife or a needle. Preferably, the tool will be sterile. For example, in a two-step procedure, an opening in the shell can first be made with a knife or other sharp instrument. In a second step, a needle attached to a syringe containing a sperm sample can be passed through the opening to deliver the sperm sample into the egg. Introduction of the sperm sample into the opening in the shell may also be accomplished by other means, including, but not limited to, the use of a pipette, such as a micropipettor. Alternatively, in one step, a needle attached to a syringe containing the sperm sample can be used to penetrate and thus create the opening in the shell and deliver by injection the sperm sample into the egg. Thus, "opening" can include a hole created by a needle. Of course, one of ordinary skill in the art will be able to choose a needle whose gauge will be large enough to allow the sperm sample to be moved through the needle. In one embodiment, the needle will be of the smallest gauge that can deliver intact sperm into the shell and also be sturdy enough to penetrate the calcium eggshell. Alternatively, a separate needle or other device could be used to make the opening in the eggshell. Typically, needles varying from 30-gauge to 16-gauge can be used. In one embodiment a 22-gauge needle is used. A sperm is approximately 0.5 um at its widest point and 100 um in length. Therefore, in a preferred embodiment, a needle with an inner diameter of at least 10 um can be used for injections. In one embodiment the needle can remain in the shell after injection. Various needles and methods now used for injection of vaccines into eggs could be used or adapted for delivery of sperm.

The egg injection mechanism may be of a design similar to those manufactured and sold by Embrex, Inc., Merck Inc., and others in the industry. As an example, one design is disclosed in U.S. Pat. No. 4,903,635, entitled "High Speed Automation Injection System for Avian Embryos," which is incorporated herein by reference. As described in the patent, the disclosed device is a high-speed automated injection system for avian embryos, which can inject eggs with fluid substances, specifically an inoculating fluid. The machine includes suction devices which lift eggs out of engagement with surfaces, rather than pushing them, before injecting them. Thus, the machine provides separate mechanisms and devices for first forming an opening in the egg shell and then injecting the avian embryo or the surrounding environment with a fluid substance, avoiding use of a single needle or punch to both puncture the shell of an egg and deliver fluid substances to the interior of the egg. As is also known in the art, the present invention here also contemplates using a single needle both to puncture the shell and to deliver fluid substances. Other relevant patents that disclose injection of fluids into eggs include U.S. Pat. No. 5,900,929, entitled "Method and Apparatus for Selectively Injecting Poultry Eggs"; U.S. Pat. No. 5,722,342, entitled "Ovo Antibiotic and Microbial Treatment to Diminish Salmonellae Populations in Avians"; U.S. Pat. No. 5,699,751, entitled "Method and Apparatus for in Ovo Injection"; U.S. Pat. No. 5,438,954, entitled "Method and Apparatus for Early Embryonic in Ovo Injection"; U.S. Pat. No. 5,339,766, "Method of Introducing Material into Eggs During Early Embryonic Development"; U.S. Pat. No. 5,176,101, "Modular Injection System for Avian Embryos"; U.S. Pat. No. 5,158,038, "Egg Injection Method, Apparatus and Carrier Solution for Improving Hatchability and Disease"; and U.S. Pat. No. 5,136,979, "Modular injection system for avian embryos," all of which are incorporated by reference. In the simplest embodiment for IOF, sperm is substituted for antigen in these machines and the depth of injection is adjusted to accomplish IOF.

The opening can be made anywhere in the shell that effects viable fertilization, but is typically made in an area of the shell that is near the germinal disc. While an egg may be manipulated so as to place the germinal disc at different regions of the egg, the germinal disc in a newly oviposited egg is located at the large end of the shell, which overlies the air cell adjacent to the yolk. Once an opening has been created in the shell, the sperm sample is preferably delivered by introducing the needle, pipette, etc., through the air cell and beneath a membrane lying below the air cell (inner shell membrane). The sperm number can be increased or decreased, depending on where and in what form the sperm are administered. In a further preferred embodiment, the sperm sample is delivered into the egg using a needle. In nature, the sperm cells must penetrate the inner perivitelline membrane and fuse with the oolema for successful fertilization to occur. With IOF, the sperm cells must also penetrate the outer perivitelline membrane before successful fertilization can occur. To increase the fertilization efficiency, one can treat the OPL. Any treatment which rendered the OPL or yolk membrane more permeable to sperm could be utilized, for example, a non-toxic acid, a proteolytic enzyme or physical abrasion.

In one embodiment, the needle, pipette, etc., is advanced through the shell at an angle of approximately 15°, penetrating the membrane lining the shell. In a method of the invention, the needle, pipette, etc., can be advanced through the air cell, until it meets the inner shell membrane. A person practicing the method of the invention will know that the tip of the needle, pipette, etc., has encountered the membrane when slight resistance to further advancement of the tip is felt. As the tip is gently advanced, the resistance from the membrane gives way and the tip is allowed to barely penetrate the membrane. The sperm sample can then be delivered into the egg, adjacent to a region of the membrane and that is adjacent to the germinal disc. Therefore, the sperm can be delivered just under the membrane, a process known as intracytoplasmic sperm injection (ICSI). Typical volumes of the sperm sample are as small as 0.005 ml or as large as 0.10 ml. A typical volume of injected sperm sample is about 0.01 ml.

Preferably, to prevent contamination of the egg and death of an embryo, the opening in the shell is sealed. A non-toxic adhesive can be applied directly to the opening in the shell to seal it. Alternatively, a piece of eggshell can be used as a patch to close the opening and may be attached to the shell with a non-toxic adhesive. In one embodiment, the non-toxic adhesive is Elmer's® glue. In another embodiment, the adhesive is silicone sealant. Moreover, any "tissue glue" can also be used to seal the shell. A "tissue glue" is a sterile, non-toxic adhesive used during surgical, operative procedures to bind tissues together.

The method of the present invention can be used to fertilize oviposited eggs from avian species selected from the group consisting of chicken, quail, duck, turkey, pheasant, ostrich, emu, goose, peafowl, grouse, rhea, parrot, cockatiel, cockatoo, parakeets, and other commercially valuable birds.

The present invention also provides a method of fertilizing an avian egg in a shell, wherein the egg comprises a yolk enclosed by a membrane, and hatching a live chick, comprising obtaining a sperm sample comprising avian sperm in a physiologically acceptable carrier, delivering the sperm sample into the egg, so as to fertilize the egg, incubating the egg, and hatching the live chick from the egg. As used herein, "obtaining" includes utilizing pre-made and pre-delivered sperm samples.

After the sperm sample has been delivered into the egg according to the methods of the present invention as described above, the egg is incubated until the live chick is hatched. One of ordinary skill will be aware of the amount of time and the preferred conditions for incubating a fertilized egg belonging to a particular species. The following are incubation periods for various species of birds: Chicken-21 days, Quail-23 days, Corunix quail-17 to 18 days, Pheasant-23 days, Turkey-28 days, Duck-28 to 33 days, Goose-28 to 30 days, Parakeet-18 days, Parrots-28 days, Dove-14 days, Mynah-14 days, Finch-14 days, Button Quail-16 days, Valley Quail-21 to 22 days, Swan-30 to 37 days. Incubation of eggs fertilized by the methods of the present invention as compared to naturally fertilized eggs may differ only in that the length of incubation time may be lengthened to include the amount of time that the fertilized egg would have spent within the body of the female prior to oviposition. In a preferred embodiment, the incubation period lasts from 21 to 23 days for chicken eggs. While one of ordinary skill in the art will readily be able to determine the optimal temperature for incubation of an egg from a particular species of bird, typically the incubation temperature is between 95° F. and 100° F. A chicken egg will be incubated at about 99.5° F. In a more preferred embodiment, the temperature at which the chicken egg is incubated will be lowered as the egg nears the point of hatching. Thus, in a currently preferred embodiment, a chicken egg is incubated at 99.5° F. from day 1 of incubation to about day 18 of incubation, and at 98.50° F. from day 19 of incubation to hatching.

As is well known in the art, the humidity level at which an egg is incubated can be important for bringing the egg to hatch. Thus, typically the egg is incubated at between 75% and 90% humidity. Preferably, the egg is incubated at about 80% humidity. More preferably, the humidity level at which the egg is incubated will be raised as the egg nears the point of hatching. Thus, in a preferred embodiment, a chicken egg is incubated at 80% humidity from day 1 of incubation to about day 18 of incubation, and at 85% humidity from day 19 of incubation to hatching. In a specific preferred embodiment, an egg is incubated at 99.5° F. and 80% humidity from day 1 of incubation to about day 18 of incubation, and at 98.50° F. and 85% humidity from day 19 of incubation to hatching. As is well known in the art, turning the eggs during incubation is useful for promoting growth of the embryo.

It is further preferred that the incubation of the eggs take place in a commercial incubator. Commercial hatchers and setters are produced by many companies including PAS Reform, Jamesway, Chickmaster, Buckeye, Cumberland, Petersime, Humidaire Incubator Co., etc. Preferably, the eggs are moved from a setter incubator to a hatcher incubator at about 3 days prior to hatch. The hatcher basket allows the egg to lie on its side where the chick can more easily pip out. This basket also allows the chick to walk about immediately after hatch, which is necessary for the chicks development and viability.

In another embodiment, the present invention provides an oviposited avian egg comprising a native embryo having fewer than 40,000 cells, wherein the embryo can develop into a live chick. "Native" means growing, living or produced in its place of origin. Thus, a native embryo is an embryo that develops and hatches the same shell in which the female pronucleus was formed. Thus, the embyro is descended from the native ovum. By the time an ovum which has been fertilized naturally has been oviposited, the developing embryo typically has between 40,000 and 70,000 cells. However, the egg of the present invention is fertilized after it has been oviposited in its shell; thus, an embryo developing in the egg of the present invention will at some time during incubation have fewer than 40,000 cells. In fact, at the moment of fertilization, the embryo in the egg of the present invention will have one cell and is a zygote. As the embryo grows within the egg, normal cell division will occur and the number of cells will increase. Thus, the fertilized, oviposited egg of the present invention will at some time during incubation comprise an embryo having, for example, 10,000, 20,000 or 30,000 cells, including less than and between these numbers of cells. Thus, the invention provides an oviposited avian egg comprising an embryo and a native yolk having fewer than 40,000, 30,000, 20,000, 10,000, 5,000, 1,000 or 100 cells, including numbers in between 1 and 40,000. Two commercially preferred avian eggs are chicken and turkey. The chicks which hatch from these eggs can have a normal karyotype and normal development.

In another embodiment, the present invention provides an avian egg in a shell comprising an embryo having fewer than 40,000 cells (e.g. 30,000; 20,000; 10,000; 1,000; 100 and 1 (zygote)), wherein the embryo can develop into a live chick, and wherein the shell has an opening of less than 4 centimeters. In another embodiment, the opening in the shell is less than 2 centimeters. In another embodiment, the opening in the shell is less than 1 centimeter or 0.5 centimeter. In one embodiment, the opening in the shell is only large enough to accommodate a 22-gauge needle. Thus, the opening can be any size between the smallest opening that will permit injection of sperm, up to smaller than the hole required to place an In Vitro fertilized (i.e., outside the shell) ovum back into the shell. By "opening" is meant a hole has been made in the egg at some point after oviposition. "Opening" includes an egg where the hole has subsequently been sealed. For example, an egg having a hole created by a needle used to inject sperm and then sealed is, even after sealing, within the definition of avian egg having an opening. The embryo can be either native or non-native to the egg. "Non-native" includes embryos developed from an ovum not native to the shell in which it was oviposited. Two commercially preferred eggs are chicken and turkey.

An egg of the present invention may, for example, be derived from avian species selected from the group consisting of chicken, quail, duck, turkey, pheasant, ostrich, emu, goose, peafowl, grouse, rhea, parrot, cockatiel, cockatoo, parakeets, swan, dove, and other commercially valuable birds. In a commercially preferred embodiment, the egg is derived from avian species used in the methods of the present invention and is selected from the group consisting of chicken, turkey, goose, duck, quail, and pheasant. In a more preferred commercial embodiment, the egg is derived from a chicken. The method can also be effectively utilized on avian species in zoos, e.g., to help preserve endangered species.

The methods of the present invention can also be used for in ovo fertilization of reptilian eggs. Reptilian eggs, similar to avian eggs, comprise a yolk and female pronucleus and are protected by a shell when they are laid. An unfertilized, oviposited reptilian egg can be fertilized in the shell according to the methods of the present invention. In particular, a sperm sample, comprising sperm from one or more reptiles of the same species, is delivered into the unfertilized, oviposited egg through an opening created in the shell and onto the yolk adjacent to the female pronucleus where fertilization occurs.

The in ovo fertilization methods described herein can also be utilized in conjunction with other in ovo procedures. For example, the embryo can be vaccinated after fertilization.

Such vaccination procedures are well known to those skilled in the art. Alternatively, such vaccination could occur simultaneous with in ovo fertilization providing however that the vaccine did not prevent development of the embryo.

Additionally, in ovo fertilization can be automated such that multiple eggs are simultaneously fertilized by, for example, injection techniques. Thus, 50, 100, 200, 300 or more eggs could be simultaneously injected.

It will be clear to those of ordinary skill in the art that the methods of the present invention may easily be applied to a large-scale industrial operation, using automation to fertilize newly laid eggs. Accordingly, apparatus which has previously been used, for example, to immunize embryos in eggs can be adapted to instead introduce a sperm sample. Any of these apparatus or other apparatus adapted for sperm injection is within the scope of applicants' invention The following Examples are set forth so as to provide those of ordinary skill in the art with a complete disclosure and description of how the methods claimed herein can be performed, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° F. and pressure is at or near atmospheric.

EXAMPLE 1

1. Forty-three freshly laid unfertilized Barred Rock chicken eggs were disinfected by wiping the shells with 3% hydrogen peroxide and placed in racks.
2. Sperm was obtained from 4 barred rock roosters on the same morning and collected in Vacutainer® vials less than 1 hour before the fertilization procedure was performed.
3. Sperm was pooled from the 4 roosters and mixed with 1 ml of Avidiluent®.
4. Sperm mixed with Avidiluent® was drawn into a 1 ml syringe through a 1", 22 gauge needle to form a sperm sample.
5. The needle was inserted and created an opening in the large, blunt end of the eggshell and passed through the opening at a 15° angle to the surface of the shell.
6. The needle was passed through the air cell until the tip just penetrated the membrane enclosing the yolk and germinal disc.
7. One drop, 0.05 ml, of the sperm sample was injected onto the surface of the yolk adjacent to the membrane.
8. The needle attached to the syringe was withdrawn from the egg.
9. The opening created in the shell by the needle was patched with a small piece of shell, and the patch was secured to the shell with Elmer's glue®.
10. The eggs were placed in commercial grade setters maintained at 99.5° F. and 80% humidity from day 1 to about day 18 of incubation. The eggs were turned according to methods known in the art and used in commercial setters.
11. On day 19, the eggs were transferred to commercial hatchers and maintained at 98.5° F. and 80% humidity until hatching.

Ten days after the fertilization method of the present invention was performed on 43 eggs, routine candling of the eggs was performed to determine which eggs had been successfully fertilized. Thirty-five eggs of the 43 eggs had been fertilized. Of the 35 fertilized eggs, 32 were successfully brought to hatching, and all but one of the chicks were healthy. Thus, 72% of the 43 oviposited eggs treated by the fertilization method of the present invention produced a healthy live chick.

EXAMPLE 2

Data on "Hy-Line Variety Brown" Commercial Brown Egg Laying Hens:
1. 270 freshly laid eggs were collected at 6:30 in the morning.
2. Semen was immediately collected from Black Giant males into diluent at a 50:50 ratio.
3. Eggs and semen were delivered to the lab within 20 minutes of semen collection.
4. Eggs were divided into two groups, experimental and negative control with 135 eggs each.
5. Experimental eggs were injected as previously described with 10 ul of the diluted semen preparation.
6. Negative controls were not injected.
7. Injected eggs were sealed with silicone sealer and placed in the incubator as previously described.
8. Fertility was checked after 5 days and recorded.
9. 33 of 135 eggs (24%) were determined to be fertile in the experimental group. None of the negative control eggs showed signs of development.

Throughout this application, various publications are referenced. The disclosures of these publications, and the references cited therein, in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

What is claimed is:

1. A method of fertilizing an oviposited avian egg in a shell, wherein the egg comprises a yolk enclosed by a membrane, comprising:
    a) obtaining a sperm sample comprising avian sperm in a physiologically acceptable carrier; and
    b) delivering the sperm sample into the egg through its shell, so as to fertilize the egg.

2. The method of claim 1, wherein the egg and the sperm are derived from a member of the same species.

3. The method of claim 1, wherein the carrier is seminal fluid.

4. The method of claim 1, wherein the carrier is diluted seminal fluid.

5. The method of claim 4, wherein the diluted seminal fluid comprises AVIDILUENT.

6. The method of claim 1, wherein the sperm sample is delivered adjacent to the membrane enclosing the yolk.

7. The method of claim 6, wherein the sperm sample is delivered adjacent to a region of the membrane that is adjacent to the germinal disc.

8. The method of claim 1, wherein the sperm sample is delivered beneath the membrane.

9. The method of claim 2, wherein the avian species is selected from the group consisting of chicken, quail, duck, turkey, pheasant, ostrich, goose, and rhea.

10. The method of claim 9, wherein the avian species is chicken.

11. The method of claim 1, wherein the sperm sample comprises a mixture of sperm obtained from more than one bird of the same species.

12. The method of claim 1, wherein the delivery of the sperm sample is achieved by making an opening in the shell by penetrating the shell and introducing the sperm sample into the egg.

13. The method of claim 12, wherein penetration and introduction are achieved with a needle.

14. The method of claim 12, wherein the opening is sealed.

15. The method of claim 14, wherein the opening is sealed with an adhesive.

16. The method of claim 1, wherein the sperm sample is delivered to multiple eggs substantially simultaneously.

17. The method of claim 16, wherein the sperm sample is delivered to at least 20 eggs.

18. The method of claim 16, wherein the sperm sample is delivered to at least 50 eggs.

19. A method of fertilizing an oviposited avian egg in a shell, wherein the egg comprises a yolk enclosed by a membrane, and hatching a live chick, comprising delivering a sperm sample comprising avian sperm in a physiologically acceptable carrier into the egg through its shell, so as to fertilize the egg in its shell and incubating the egg until hatching.

20. The method of claim 19, wherein the egg and the sperm are derived from a member of the same species.

21. The method of claim 19, wherein the carrier is seminal fluid.

22. The method of claim 19, wherein the carrier is diluted seminal fluid.

23. The method of claim 22, wherein the diluted seminal fluid comprises AVIDILUENT.

24. The method of claim 19, wherein the sperm sample is delivered adjacent to the membrane enclosing the yolk.

25. The method of claim 24, wherein the sperm sample is delivered adjacent to a region of the membrane that is adjacent to a germinal disc.

26. The method of claim 19, wherein the sperm sample is delivered beneath the membrane.

27. The method of claim 19, further comprising treating the membrane so as to increase fertilization compared to fertilization in the egg with an untreated membrane.

28. The method of claim 19, wherein the avian species is selected from the group consisting of chicken, quail, duck, turkey, pheasant, ostrich, goose, and rhea.

29. The method of claim 28, wherein the avian species is chicken.

30. The method of claim 19, wherein the sperm sample comprises a mixture of sperm obtained from more than one bird.

31. The method of claim 19, wherein the delivery of the sperm sample is achieved by making an opening in the shell by penetrating the shell and introducing the sperm sample into the egg.

32. The method of claim 31, wherein penetration and introduction are achieved with a needle.

33. The method of claim 31, wherein the opening is sealed.

34. The method of claim 33, wherein the opening is sealed with an adhesive.

35. The method of claim 19, wherein the sperm sample is delivered to multiple eggs substantially simultaneously.

36. The method of claim 35, wherein the sperm sample is delivered to at least 20 eggs.

37. The method of claim 35, wherein the sperm sample is delivered to at least 50 eggs.

38. The method of claim 19, wherein the egg is a chicken egg, and incubation of the egg lasts from 21 to 23 days.

39. The method of claim 38, wherein incubation is performed at a temperature of about 99.5° F. from day 1 to about day 18 of incubation and a temperature of about 98.5° F. from about day 19 of incubation to hatching.

40. The method of claim 38, wherein incubation is performed at 80% humidity from day 1 to hatching.

41. The method of claim 19, further comprising vaccinating the egg during incubation.

42. A method of fertilizing a chicken egg in a shell, wherein the egg comprises a yolk enclosed by a membrane, comprising:
   a) obtaining a chicken sperm sample in a physiologically acceptable carrier; and
   b) delivering the sperm sample into the egg through its shell, so as to fertilize the egg.

43. A method of fertilizing a chicken egg in a shell, wherein the egg comprises a yolk enclosed by a membrane comprising:
   a) obtaining diluted chicken sperm; and
   b) delivering the diluted sperm into the egg through its shell, so as to fertilize the egg.

44. A method of fertilizing a chicken egg in a shell, wherein the egg comprises a yolk enclosed by a membrane comprising:
   a) obtaining diluted chicken sperm; and
   b) delivering the diluted sperm into the egg in its shell by penetrating the shell and introducing the diluted sperm into the egg.

45. A method of fertilizing a chicken egg in a shell, wherein the egg comprises a yolk enclosed by a membrane comprising:
   a) obtaining diluted chicken sperm; and
   b) delivering the diluted sperm into the egg in its shell adjacent to a region of the membrane that is adjacent to the germinal disc, by penetrating the shell and introducing the diluted sperm into the egg.

46. A method of fertilizing an oviposited chicken egg in a shell, wherein the egg comprises a yolk enclosed by a membrane, and hatching a live chick, comprising delivering a chicken sperm sample in a physiologically acceptable carrier into the egg through its shell, so as to fertilize the egg and incubating the egg until hatching.

47. A method of fertilizing an oviposited chicken egg in a shell, wherein the egg comprises a yolk enclosed by a membrane, and hatching a live chick, comprising delivering diluted chicken sperm into the egg through its shell, so as to fertilize the egg and incubating the egg until hatching.

48. A method of fertilizing an oviposited chicken egg in a shell, wherein the egg comprises a yolk enclosed by a membrane, and hatching a live chick, comprising delivering diluted chicken sperm into the egg in its shell by penetrating the shell and introducing the diluted sperm into the egg, so as to fertilize the egg and incubating the egg until hatching.

49. A method of fertilizing an oviposited chicken egg in a shell, wherein the egg comprises a yolk enclosed by a membrane, and hatching a live chick, comprising delivering diluted chicken sperm into the egg in its shell adjacent to a region of the membrane that is adjacent to the germinal disc by penetrating the shell and introducing the diluted sperm into the egg, so as to fertilize the egg and incubating the egg until hatching.

* * * * *